(12) United States Patent
Berg

(10) Patent No.: US 11,761,871 B2
(45) Date of Patent: Sep. 19, 2023

(54) METHOD FOR DETERMINING LUBRICANT PROPERTIES

(71) Applicant: Schaeffler Technologies AG & Co. KG, Herzogenaurach (DE)

(72) Inventor: Franziska Berg, Oberhaid (DE)

(73) Assignee: Schaeffler Technologies AG & Co. KG, Herzogenaurach (DE)

(*) Notice: Subject to any disclaimer, the term of this patent is extended or adjusted under 35 U.S.C. 154(b) by 194 days.

(21) Appl. No.: 17/294,544

(22) PCT Filed: Aug. 6, 2019

(86) PCT No.: PCT/DE2019/100710
§ 371 (c)(1),
(2) Date: May 17, 2021

(87) PCT Pub. No.: WO2020/103969
PCT Pub. Date: May 28, 2020

(65) Prior Publication Data
US 2022/0018749 A1     Jan. 20, 2022

(30) Foreign Application Priority Data
Nov. 22, 2018 (DE) .................... 10 2018 129 457.3

(51) Int. Cl.
*G01N 33/00* (2006.01)
*G01N 11/02* (2006.01)
*G01N 33/30* (2006.01)

(52) U.S. Cl.
CPC ............. *G01N 11/02* (2013.01); *G01N 33/30* (2013.01)

(58) Field of Classification Search
CPC ...... G01N 11/02; G01N 33/30; G01N 11/142; G01N 2011/0026; G01N 11/00; G01N 33/00
(Continued)

(56) References Cited

U.S. PATENT DOCUMENTS

| 6,571,610 B1 | 6/2003 | Raffer |
| 2005/0132783 A1 | 6/2005 | Reinheimer et al. |

(Continued)

FOREIGN PATENT DOCUMENTS

| CN | 105910958 A | 8/2016 |
| DE | 19650616 A1 | 6/1998 |

(Continued)

OTHER PUBLICATIONS

DIN standard 51810-2 published Apr. 2017 titled "Prüfung von Schmierstoffen—Prüfung der rheologischen Eigenschaften von Schmierfetten—Teil 2: Bestimmung der Fließgrenze mit dem Oszillationsrheometer und dem Messsystem Platte/Platte".

(Continued)

*Primary Examiner* — Robert R Raevis

(57) ABSTRACT

A method for determining a suitability of a lubricant to avoid false brinelling damage in a bearing includes providing a rheometer and the lubricant, performing a first conditioning of the rheometer, filling the rheometer with a first lubricant sample, and deforming the first lubricant sample to determine a first shear stress from a first shear deformation of the first lubricant sample at the first temperature, with reference to the first zero point. The method also includes performing a second conditioning of the rheometer, refilling the rheometer with a second lubricant sample, and deforming the second lubricant sample to determine a second shear stress from a second shear deformation of the second lubricant sample at the second temperature, with reference to the second zero point. The lubricant is classified as suitable or unsuitable for avoiding false brinelling damage as a function of the first shear stress and the second shear stress.

10 Claims, 3 Drawing Sheets

(58) Field of Classification Search
USPC ............... 374/45, 46, 47, 54; 73/10, 53.05
See application file for complete search history.

(56) References Cited

U.S. PATENT DOCUMENTS

| | | | | |
|---|---|---|---|---|
| 2012/0123373 A1* | 5/2012 | Melik | ............... | A61L 15/24 |
| | | | | 604/372 |
| 2014/0193110 A1 | 7/2014 | Soga et al. | | |

FOREIGN PATENT DOCUMENTS

| | | | | |
|---|---|---|---|---|
| DE | 19650616 | C2 | 9/2001 | |
| DE | 10350554 | A1 | 6/2005 | |
| DE | 112014005236 | T5 | 9/2016 | |
| EP | 0461704 | A1 | 12/1991 | |
| JP | H04232440 | A | 8/1992 | |
| JP | 2006132619 | A | 5/2006 | |
| JP | 2006177734 | A | 7/2006 | |
| JP | 2013082882 | A | 5/2013 | |
| JP | 2015524489 | A | 8/2015 | |
| JP | 2015172153 | A | 10/2015 | |
| JP | 2015224255 | A | 12/2015 | |
| SU | 1388741 | A1 | 4/1988 | |
| WO | WO-2018011392 | A1 * | 1/2018 | ............. A23C 21/00 |

OTHER PUBLICATIONS

Cornelia Küchenmeister-Lehrheuer und Klaus Oldörp, thermoscientific publication Nr. V-248 titled "Gute Vorbereitung-gute Messergebnisse", May 3, 2023.

* cited by examiner

METHOD FOR DETERMINING LUBRICANT PROPERTIES

CROSS-REFERENCE TO RELATED APPLICATIONS

This application is the United States National Phase of PCT Appln. No. PCT/DE2019/100710 filed Aug. 6, 2019, which claims priority to German Application No. DE102018129457.3 filed Nov. 22, 2018, the entire disclosures of which are incorporated by reference herein.

TECHNICAL FIELD

The disclosure relates to a method for determining lubricant properties. In particular, the disclosure relates to a method for determining the suitability of a lubricant, especially a lubricating grease for avoiding false brinelling damage patterns (also referred to as a special form of corrugation) in grease-lubricated roller bearings.

BACKGROUND

In roller or ball bearings, lubricants form a film between lubricating surfaces and thus prevent direct contact between surfaces moving against one another. In this way, mechanical friction and wear are reduced. The properties of lubricating greases in terms of their viscosity depend heavily on the temperature range in which they are used. Their suitability as a lubricant also depends on the speed at which the surfaces move relative to one another. At higher speeds, the lubricant heats up more and can reach a temperature at which it decomposes. At low temperatures, due to the higher viscosity of the lubricant; the flow into the space between the surfaces can take place so slowly that the film between the lubricating surfaces breaks.

The lubrication of roller bearings should primarily fulfill two goals: minimizing friction and protecting against wear. During the normal operation of roller bearings, a distinction is made between different lubrication conditions in which, depending on the speed of the bearing, so-called "fully supporting lubricating films" can form. Depending on the properties of the lubricant, the formation of fully supporting lubricating films is encouraged. One of the key parameters is the viscosity of the lubricant. A particular problem arises when new roller bearings freshly filled with lubricant are transported. This affects, for example, car wheel bearings during vehicle transport on motorail trains or on truck transporters. Here, especially with the double row angular contact ball bearings, there are repeated damage patterns that show damage to the inner and outer ring raceways at the positions of the loaded balls. This damage to the inner and outer ring raceways can reach depths of several microns and, without closer microscopic examination, initially appear like indentations caused by the balls. Such damage patterns can be based on what is known as "false brinelling".

The anti-false brinelling property of lubricants, i.e., the ability to prevent the damage described above, is normally determined in time-consuming and expensive test bench tests. Characteristic values of lubricants are determined in a rheological test stand or measuring device. Essentially two rheological methods for testing lubricants based on DIN51810-2 are used as laboratory test methods. DIN51810-2 describes how the measuring process is structured, which devices are used and which rheological parameters can be determined by the measurement.

SUMMARY

The disclosed method provides a simple and inexpensive method with which the suitability of a lubricant, e.g., a lubricating grease, for avoiding false brinelling damage in a bearing can be quickly determined.

Investigations have shown that typical false brinelling damage is by no means due to static overloading of the raceway material by the rolling elements. Rather, this type of damage occurs through the interaction of several influencing factors. These are a highly stressed point contact in the grease-lubricated roller bearing, a basically stationary bearing, which, however, experiences a micro-movement of about ±1° in the radial direction and low outside temperatures of −20° C. or lower. It has been found that false brinelling damage occurs, for example, when the rolling elements/balls in the load zone of a bearing displace not only the existing lubricant but, above all, the free base oil of the lubricating grease from the contact area and, due to the temperature-related high viscosity, do not move it quickly enough the contact area can flow back. This can lead to an almost unlubricated rolling contact, which can cause wear and corrosion. The resulting surface damage, which occurs at the distance between the rolling elements on the bearing surfaces, is referred to as false brinelling damage and can be reduced by changing the composition of the lubricants or by selecting the appropriate lubricants.

The disclosure is essentially based on the knowledge that the rheological parameters of an examined lubricant to be determined at at least two different, preselected temperatures provide information about the suitability of the lubricant for avoiding false brinelling damage in a bearing in the temperature range between the two temperatures and possibly also enable it. For this purpose, the measured parameters at the two temperatures are entered together in a value field (diagram or table of values), and an indication or a signal is generated from the position of the resulting value pair in the value field, which is representative of the suitability of the lubricant for avoiding false brinelling damage in a warehouse. In the context of the present disclosure, a lubricant may be understood to be a lubricating grease, as is typically used in bearings.

In order to be able to compare the results obtained in this way with results such as those obtained in conventional methods, the method according to the disclosure may have a conversion step in which conversion factors are used.

The method according to the disclosure for determining the suitability of a lubricant, e.g., a lubricating grease, for avoiding false brinelling damage in a bearing has the following steps:

conditioning of a rheometer with the sub-steps:
 a) Equilibrating the rheometer to a first temperature,
 b) Setting of a first zero point after a specified first temperature check time of the rheometer has elapsed,
filling of the rheometer with a lubricant sample,
deformation of the lubricant sample and determining the first shear stress from the shear deformation of the lubricant sample at the first temperature;
conditioning of a rheometer with the sub-steps:
 c) Equilibrating the rheometer to a second temperature,
 d) Setting of a second zero point after a specified second temperature check time of the rheometer has elapsed,
filling of the rheometer with a lubricant sample,
deformation of the lubricant sample and determination of the second shear stress from the shear deformation of the lubricant sample at the second temperature, Classifying the lubricant as suitable or unsuitable for avoiding false brinelling damage in a bearing as a function of the determined first shear stress and the determined second shear stress.

Meaningful temperature values found for assessing a lubricant, e.g., a lubricating grease, with regard to its suitability for avoiding false brinelling damage in a bearing are the lowest temperature to be assumed when the lubricant is used in the field and, for example, the usual temperature when the lubricant is introduced into the warehouse. Therefore, in the method to be carried out, the first temperature may be selected in the range of −45° C. to −5° C. and the second temperature may be selected in the range of +20° C. to +50° C. For example, the method may be carried out at the first temperature of −30° C. and at the second temperature of +25° C.

In numerous tests it has been found that the suitability of the lubricant for avoiding false brinelling damage in a bearing is very good if the first shear stress is up to 1000 Pa at the first temperature and the second shear stress up to 100 Pa at the second temperature. It is suitable if the first shear stress is up to 1750 Pa and the second shear stress is up to 275 Pa. The lubricant is only of limited use if the first shear stress is up to 2500 Pa and the second shear stress is up to 375 Pa. The lubricant is poorly suited from the point of view of avoiding false brinelling damage if the first shear stress is above 2500 Pa and the second shear stress is above 375 Pa.

Since deviations occur in the individual measurements, to improve the statistical error the method may be carried out with two, three or more measurements for each measured value.

The method can be carried out quickly and without a large outlay in terms of equipment, so that a lubricant can be quickly assessed, e.g., in terms of its suitability as a lubricant to avoid false brinelling damage in a bearing.

BRIEF DESCRIPTION OF THE DRAWINGS

Further features and advantages of the disclosure will be apparent from the following description of example embodiments, with reference to the accompanying drawings. In the figures.

DETAILED DESCRIPTION

Figure 1:
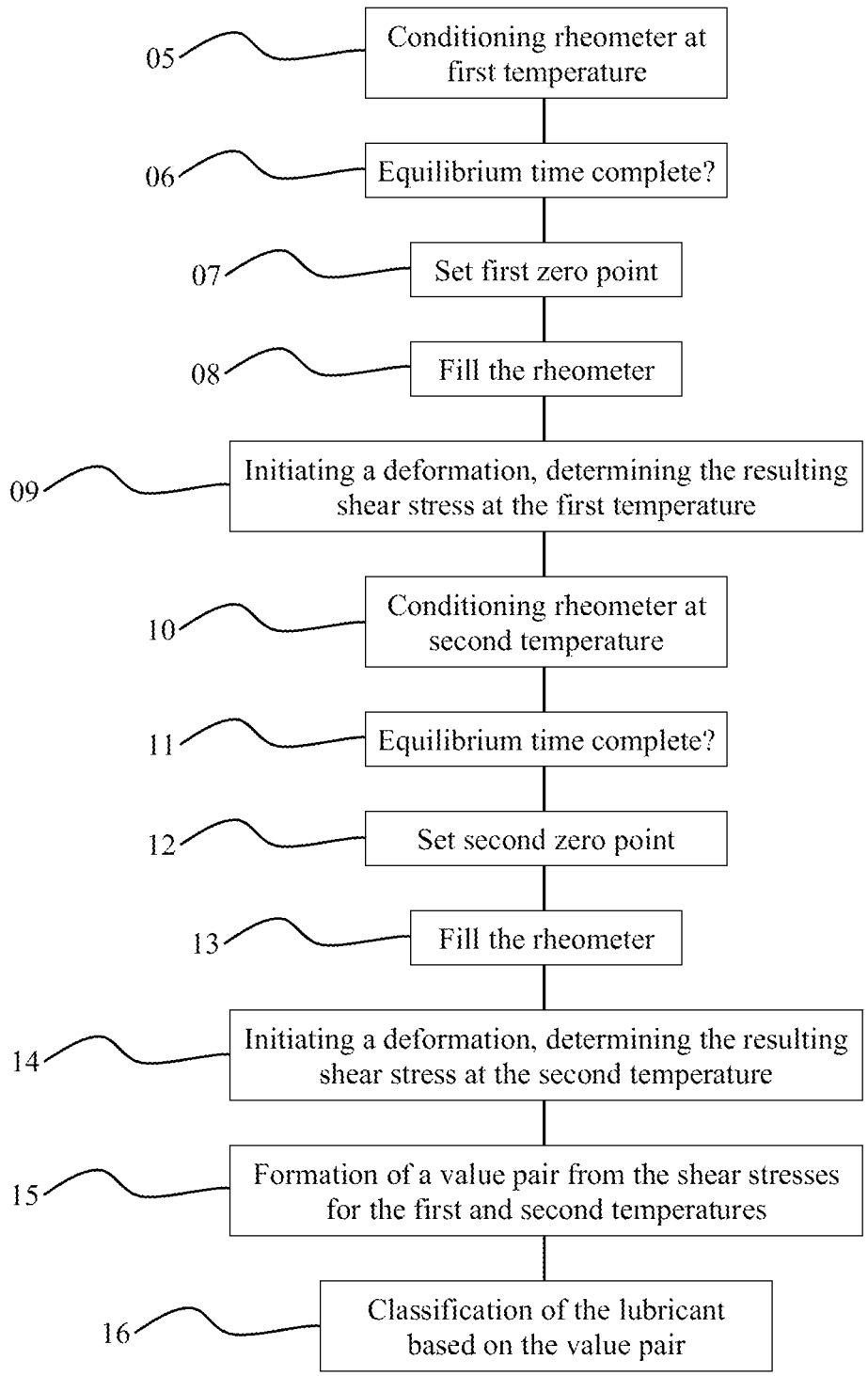
FIG. 1 shows a flow chart of an embodiment of the method according to the disclosure.

FIG. 1 shows a flow chart of a method according to the disclosure for determining the suitability of a lubricant, e.g., a lubricating grease, for avoiding false brinelling damage in a bearing with the following method steps: In a first step 05, a rheometer is conditioned to determine the flow properties of a lubricant at a first temperature. To do this, the rheometer is brought to the first temperature. The rheometer is held at this first temperature in step 06 for a predetermined temperature equilibration time. During this period the rheometer relaxes, i.e., a temperature gradient should no longer be present in the rheometer after the temperature equilibration time. During this temperature equilibration time (also referred to as the settling time or relaxation time), a continuous check is made in step 06 to determine whether the temperature equilibration time has already expired and whether the next step can be initiated.

When the temperature equilibration time has expired, the rheometer is adjusted, i.e., a first zero point is set in step 07, to which the further rheological measurements at the first temperature relate.

The rheological measurement begins with the rheometer being filled with a lubricant sample (lubricating grease) in step 08. In step 09, a predetermined shear deformation is exerted on the lubricant sample so that the lubricant sample is deformed in the rheometer. In addition to the size of the shear deformation and the applied shear stress, other rheological parameters of the examined lubricant, such as the storage and loss modulus, are determined at the respective measuring temperature. Fundamentally, rheological measurements are known to the person skilled in the art, so that an explanation of details can be dispensed with here.

The lubricant sample is now removed from the rheometer in order to then carry out a second conditioning at a second temperature in step 10. In step 10, the rheometer is brought to the second temperature for this purpose. In step 11 compliance with a second temperature equilibration time is monitored, and in step 12 a second zero point is set to which the further rheological measurements at the second temperature relate.

After this second conditioning and a renewed filling of the rheometer with a further sample of the same lubricant in step 13, the rheological investigations can be carried out at the second temperature. In step 14, a predetermined shear deformation is exerted on the further lubricant sample and the shear stress is determined.

The specific shear stress at the first temperature and the specific shear stress at the second temperature are both taken into account for the subsequent determination of the suitability of the lubricant for avoiding false brinelling damage in a bearing. First, the recorded shear deformation is converted into a shear rate and the associated shear stress is determined for this, whereupon value pairs are formed in step 15. Such a value pair thus includes a shear stress value at the first temperature and a shear stress value at the second temperature. The value pair defines a position in a two-dimensional value field, this position being a measure of the suitability of the lubricant for avoiding false brinelling damage in a bearing in which the lubricant is to be used.

For a better understanding of the disclosure, this value field can be shown as a diagram in which the value pairs for different lubricants are entered, with the shear stress at the first temperature being plotted on the x-axis and the shear stress at the second temperature on the y-axis.

Using the value pair, i.e., from the position of the value pair in the value field, the suitability of the lubricant for avoiding false brinelling damage in a bearing is determined in step 16, the first shear stress and the second shear stress being included in the evaluation.

Specific examples for recording measured values and their classification according to the method of the disclosure are explained below.

Preparations and Measurement at −30° C.=First Temperature

At the beginning, the rheometer including the measuring system is equilibrated to −30° C. After a temperature equilibration time of approx. 30 minutes has elapsed, the first zero point is set. Since −30° C. is well below room temperature, the rheometer is brought to room temperature again after setting the first zero point and before applying the lubricant sample in order to avoid condensation of water vapor and rime formation below 0° C. After the rheometer has been brought back to room temperature, it is filled with the lubricant sample. Then the measuring system starts with the lubricant sample chilled to −30° C. Once −30° C. is reached, this temperature is kept constant for approx. 30 minutes to ensure that the measuring system as well as the lubricant sample actually have the first temperature of −30° C. An amplitude sweep is now carried out to determine the shear stress at the first temperature. The shear deformation is increased from 0.01% to 1000%. The first part of the measurement is now finished, so the rheometer can be emptied and cleaned.

Preparations and Measurement at +25° C.=Second Temperature

At the beginning the rheometer including the measuring system is equilibrated to +25° C. After a temperature equilibration time of approx. 5 minutes has elapsed, the second zero point is set. The rheometer is then refilled with a sample of the same lubricant. The measuring system and the sample are equilibrated to +25° C. and then a second amplitude sweep is carried out to determine the second shear stress. The shear deformation is increased from 0.01% to 1000%. This ends the measurement and the measured values are processed further.

In the example described above, the rheological variables are determined once at −30° C. (first temperature) and once at +25° C. (second temperature) in an amplitude sweep. In the amplitude sweep, the shear deformation of the lubricant is varied between 0.01% and 1000%. The amplitude is changed at a constant frequency of 10 rad/s and increases by powers of ten. The measured values can be recorded on a logarithmic scale with 5 or 10 or 20 points per decade, for example. The applied shear deformation is specified as part of the measurement. From this specification and the measured value, the shear stress can be determined in a manner known in and of itself, taking into account further device constants and material values.

For this purpose, when evaluating the amplitude sweep at +25° C., the shear stress value at a shear rate of 0.36 s$^{-1}$ is determined using the measurement data. In the amplitude sweep at −30° C., the recorded shear deformation is first converted into a shear rate in the same way and a shear stress value is then determined for this, for example from a stored table of values or with the help of an implemented mathematical relationship. From the characteristic value at +25° C. and the characteristic value at −30° C. a value pair is formed. This value pair defines a position in a value field; the value field can be stored, for example, in a memory or can also be described by a mathematical function which can be executed by software. For clarification, the pair of values can also be automatically entered in a diagram, which is displayed or printed out, for example.

The position of the value pair in the value field is a measure of whether the examined lubricant has good or bad anti-false brinelling properties. Furthermore, from the value pair of the two shear stress values, it is not only possible to determine whether there are good or bad anti-false brinelling properties, but also to what extent.

With the method according to the disclosure, lubricants, e.g., lubricating greases, whose anti-false brinelling properties can be attributed to good flow properties can be examined. To determine the anti-false brinelling properties of a grease down to −30° C. by means of a rheological process, the measuring system may be first cleaned with technical ethanol, denatured alcohol, isopropanol, technical acetone or industrial spirit. The measuring system comprises a rheometer with a Peltier plate, a plate measuring system for rheometers, with a size of Ø25 mm, for example. In addition to the Peltier plate, a temperature-controlled cover hood may be used for the measuring system in order to bring the measuring system to the desired temperature. If a Peltier element is used, it must be counter-cooled. A cryostat or thermostat may be used for this. After cleaning, the measuring system is filled with a lubricant sample, for example using a spatula.

When filling the measuring system, a sufficient amount of the lubricant of approx. 0.5 g with a small excess is applied to the center of the lower plate. The upper plate is then lowered to a distance of 1.025 mm, the so-called trim position, from the lower plate and excess lubricant is removed with the aid of a spatula. Then the final measuring position of 1,000 mm can be approached. During trimming, no lubricants may be removed from the measuring gap, otherwise the gap will not be filled correctly and the measured values will be falsified.

The actual measurement takes place at the respective temperature. Understandably, it is irrelevant whether the lower or the higher temperature is selected as the first measurement temperature. Two or more measurements may be carried out per measurement temperature. In this way, the statistical error of the measurements can be reduced.

To evaluate the measurements and to provide information about the suitability of the lubricating grease as an anti-false brinelling lubricant, the measured values of the shear deformation are converted into shear rates. To determine the characteristic value of the examined lubricant, the measured values for the shear deformation γ are converted into a shear rate dγ/dt according to the following equation:

$$d\gamma/dt\text{(calculated)}=\gamma\text{(measured)}*0.071$$

or, described in words:

calculated shear rate=measured shear deformation times 0.071.

Then that measured value may be sought for which the calculated shear rate is 0.36 s$^{-1}$, and the associated shear stress value is read off or determined automatically from a value field.

The two characteristic values determined are combined as a pair of values and used to determine suitability as an anti-false brinelling lubricant by evaluating the position of the pair of values in a value field. This evaluation can be carried out by comparing the value pair with a value field which is stored in a memory or on the basis of a mathematical relationship that can be mapped using software.

Figure 2:
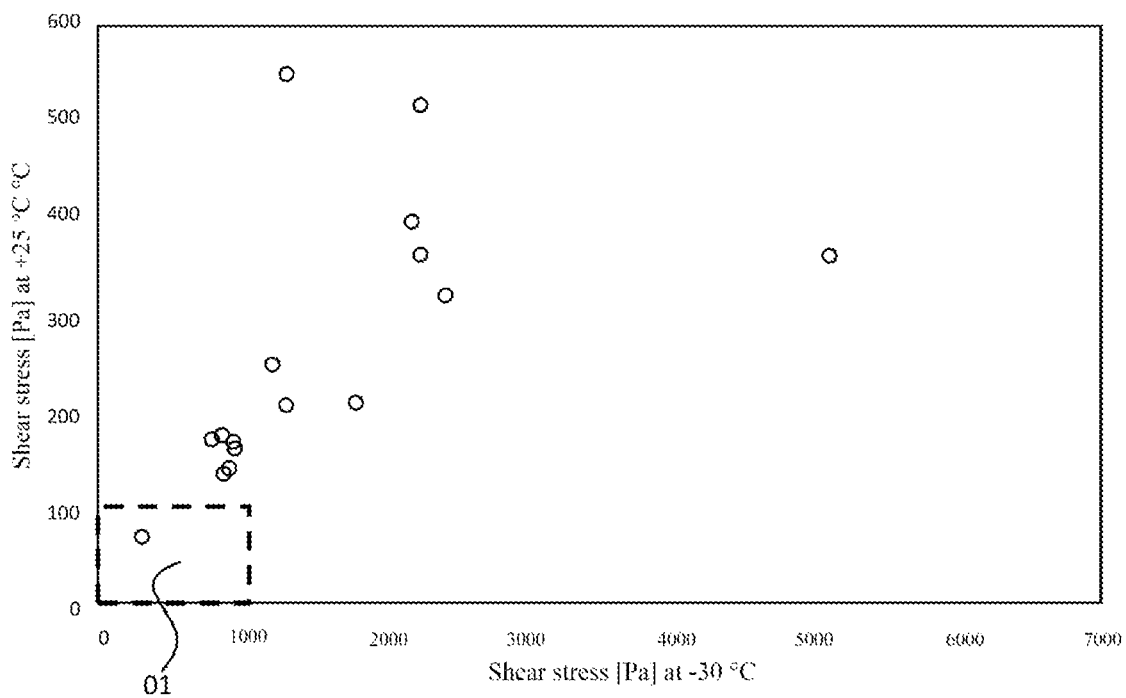
FIG. 2 shows a diagram with measured values which were obtained in a first measurement.

This determination of the position of the pair of values can be illustrated with the aid of diagrams as shown in FIGS. 2 to 5. In FIG. 2, the characteristic value of the lubricating grease at −30° C. is plotted as the horizontal axis, and the characteristic value of the lubricating grease at +25° C. is plotted as the vertical axis. Depending on the position of the pair of values in the diagram or value field, the anti-false brinelling property of the grease is classified as very good, good, marginal or unsuitable.

In FIGS. 2 to 5, the measured value pairs are each shown as open circles in the diagram. The respective range limits for the classification are also shown. In FIG. 2, a pair of values falls into an inner region 1, which contains pairs of values up to 1000 Pa at −30° C. and 100 Pa at +25° C. Lubricants whose value pairs fall into this area 1 are classified as "very good" for avoiding false brinelling damage.

Figure 3:
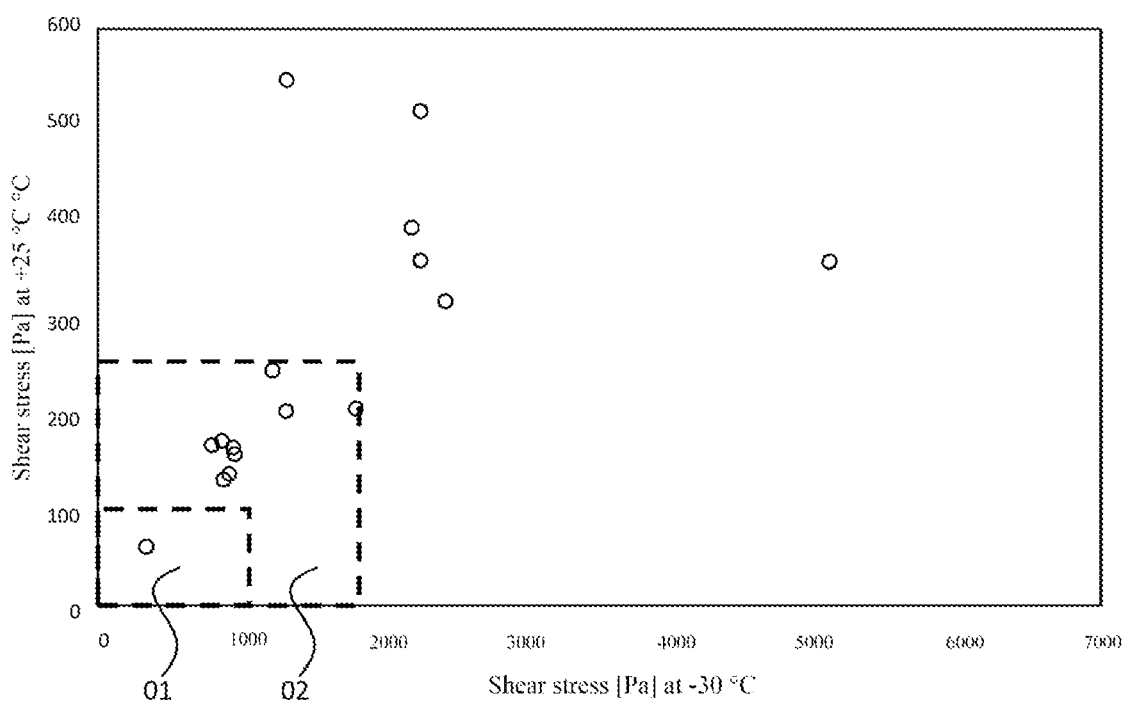
FIG. 3 shows a diagram with measured values that were obtained in a second measurement.
Figure 4:
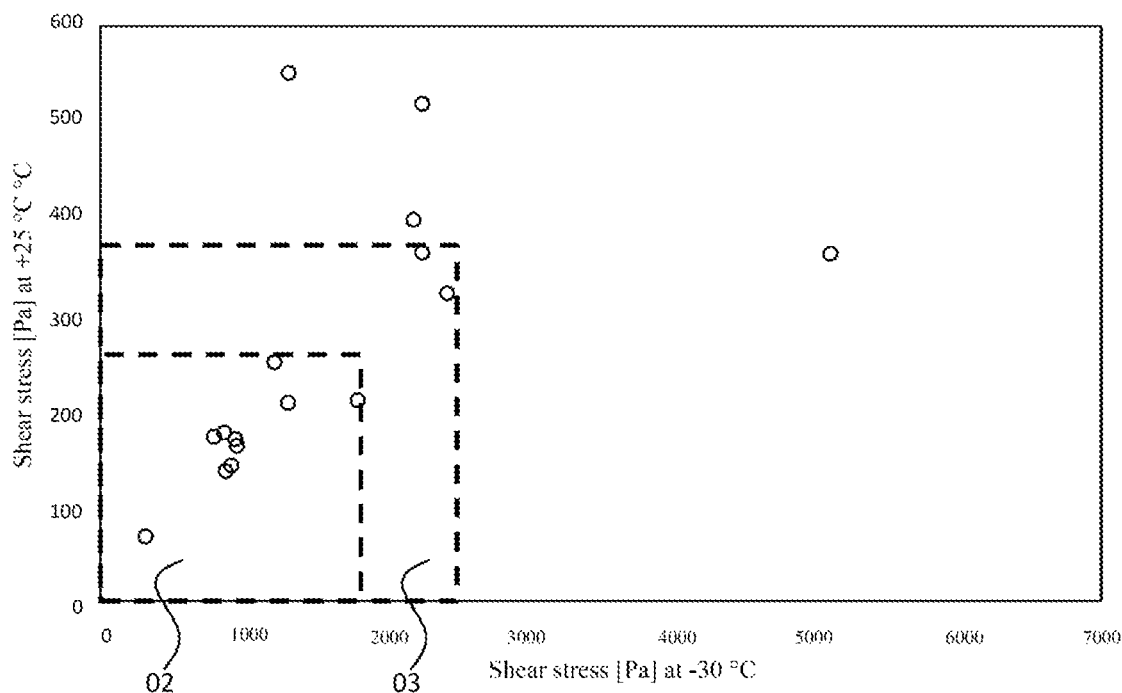
FIG. 4 shows a diagram with measured values that were obtained in a third measurement.

In addition to the area 1 with the area limits 1000 Pa at −30° C. and 100 Pa at +25° C., FIG. 3 shows a second area 2 with the area limits 1750 Pa at −30° C. and 275 Pa at +25° C. Lubricants whose value pairs fall into this area 2 are classified as "good" for avoiding false brinelling damage. In the example shown in FIG. 3, nine value pairs meet this condition. FIG. 4 shows a third area 3 with the area limits 2500 Pa at −30° C. and 375 Pa at +25° C. Lubricants whose value pairs fall into this area 3 are classified as "still conditionally suitable" for avoiding false brinelling damage. In the example shown, two pairs of values meet this condition.

Figure 5:
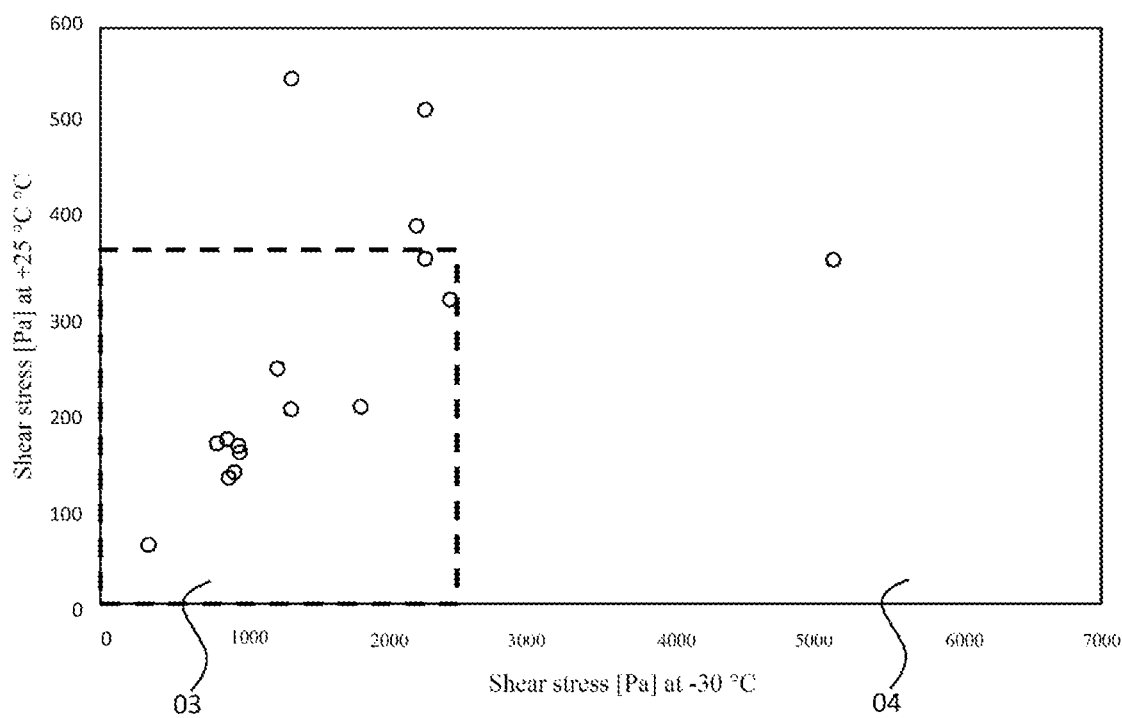
FIG. 5 shows a diagram with measured values that were obtained in a fourth measurement.

FIG. 5 shows, as a fourth area 4, the area above 2500 Pa at −30° C. and 375 Pa at +25° C. Lubricants whose value pairs fall into this range are classified as "insufficient" for avoiding false brinelling damage. In the example shown, there are four value pairs.

REFERENCE NUMERALS

01 First area="very good"
02 Second area="good"
03 Third area="still conditionally suitable"
04 Fourth area="not sufficient"
05-16 process steps

The invention claimed is:

1. A method for determining a suitability of a lubricant to avoid false brinelling damage in a bearing, comprising:
   providing a rheometer and the lubricant;
   performing a first conditioning of the rheometer, the first conditioning comprising:
      equilibrating the rheometer to a first temperature;
      waiting for a predetermined first temperature equilibrium time of the rheometer; and
      determining a first zero point;
   filling the rheometer with a first lubricant sample of the lubricant;
   deforming the first lubricant sample to determine a first shear stress from a first shear deformation of the first lubricant sample at the first temperature, with reference to the first zero point;
   performing a second conditioning of the rheometer, the second conditioning comprising:
      equilibrating the rheometer to a second temperature;
      waiting for a predetermined second temperature equilibrium time of the rheometer; and
      determining a second zero point;
   refilling the rheometer with a second lubricant sample of the lubricant;
   deforming the second lubricant sample to determine a second shear stress from a second shear deformation of the second lubricant sample at the second temperature, with reference to the second zero point; and
   classifying the lubricant as suitable or unsuitable for avoiding false brinelling damage as a function of the first shear stress and the second shear stress.

2. The method of claim 1 wherein the lubricant is a lubricating grease.

3. The method of claim 1 wherein the first temperature is −30° C. and the second temperature is +25° C.

4. The method of claim 3 further comprising:
   classifying the lubricant as "very good" if the first shear stress is 1000 Pa or less, and the second shear stress is 100 Pa or less;
   classifying the lubricant as "good" if the first shear stress is 1750 Pa or less, and the second shear stress is 275 Pa or less;
   classifying the lubricant as "conditionally suitable" if the first shear stress is 2500 Pa or less, and the second shear stress is 375 Pa or less; and
   classifying the lubricant as "bad" if the first shear stress is greater than 2500 Pa, and the second shear stress is greater than 375 Pa.

5. The method of claim 1 wherein the rheometer is empty during the first conditioning and the second conditioning.

6. The method of claim 1, further comprising providing a Peltier plate and a cover hood, wherein equilibrating the rheometer to a first temperature and equilibrating the rheometer to a second temperature are performed using the Peltier plate and the cover hood.

7. The method of claim 1 wherein:
   deforming the first lubricant sample comprises a first amplitude sweep, the first amplitude sweep comprising:
      changing the first shear deformation at a constant frequency of 10 rad/s; and
      varying the first shear deformation between 0.01% and 1000%, whereby a maximum amplitude within 10 points is increased by a factor of ten in each case; or
   deforming the second lubricant sample comprises a second amplitude sweep, the second amplitude sweep comprising:
      changing the second shear deformation at a constant frequency of 10 rad/s; and
      varying the second shear deformation between 0.01% and 1000%, whereby a maximum amplitude within 10 points is increased by a factor of ten in each case.

8. The method of claim 1, wherein the equilibrating the rheometer is conducted at a predetermined heating rate over a predetermined duration.

9. The method of claim 1, wherein:
   determining the first shear stress comprises converting a first shear deformation $\gamma$ into a first shear rate $d\gamma/dt$ and determining the first shear stress from the first shear rate; or
   determining the second shear stress comprises converting a second shear deformation $\gamma$ into a second shear rate $d\gamma/dt$ and determining the second shear stress from the second shear rate.

10. A method for determining a suitability of a lubricant to avoid false brinelling damage in a bearing, comprising:
   providing a rheometer and the lubricant;
   performing a first conditioning of the rheometer, the first conditioning comprising:
      equilibrating the rheometer to a first temperature;
      waiting for a predetermined first temperature equilibrium time of the rheometer; and
      determining a first zero point;
   filling the rheometer with a first lubricant sample of the lubricant;
   deforming the first lubricant sample to determine a first shear stress from a first shear deformation of the first lubricant sample at the first temperature, with reference to the first zero point;
   filling the rheometer with a second lubricant sample of the lubricant;
   deforming the second lubricant sample to determine a second shear stress from a second shear deformation of the second lubricant sample at the first temperature, with reference to the first zero point;
performing a second conditioning of the rheometer, the second conditioning comprising:
  equilibrating the rheometer to a second temperature;
  waiting for a predetermined second temperature equilibrium time of the rheometer; and
  determining a second zero point;
refilling the rheometer with a third lubricant sample of the lubricant;
deforming the third lubricant sample to determine a third shear stress from a third shear deformation of the third lubricant sample at the second temperature, with reference to the second zero point;
filling the rheometer with a fourth lubricant sample of the lubricant;
deforming the fourth lubricant sample to determine a fourth shear stress from a fourth shear deformation of the fourth lubricant sample at the second temperature, with reference to the second zero point;
calculating a first average shear stress from the first shear stress and the second shear stress, and calculating a second average shear stress from the third shear stress and the fourth shear stress; and
classifying the lubricant as a function of the first average shear stress and the second average shear stress.

* * * * *